US010864289B1

(12) United States Patent
Killingsworth et al.

(10) Patent No.: US 10,864,289 B1
(45) Date of Patent: Dec. 15, 2020

(54) STORAGE UNIT FOR A PLUNGER

(71) Applicants: Sequaria Killingsworth, Fort Worth, TX (US); Eddie D Killingsworth, Jr., Fort Worth, TX (US)

(72) Inventors: Sequaria Killingsworth, Fort Worth, TX (US); Eddie D Killingsworth, Jr., Fort Worth, TX (US)

(*) Notice: Subject to any disclaimer, the term of this patent is extended or adjusted under 35 U.S.C. 154(b) by 26 days.

(21) Appl. No.: 16/502,416

(22) Filed: Jul. 3, 2019

(51) Int. Cl.
A61L 2/10 (2006.01)
A47K 17/00 (2006.01)

(52) U.S. Cl.
CPC ............ *A61L 2/10* (2013.01); *A47K 17/00* (2013.01); *A61L 2202/11* (2013.01)

(58) Field of Classification Search
USPC .................................... 250/455.11
See application file for complete search history.

(56) References Cited

U.S. PATENT DOCUMENTS

| 3,458,951 | A | * | 8/1969 | Martin | A01G 31/06 47/60 |
|---|---|---|---|---|---|
| 4,008,933 | A | | 2/1977 | Wanek | |
| 4,033,650 | A | | 7/1977 | Alissandratos | |
| 4,613,996 | A | * | 9/1986 | Chase | A47D 5/003 5/135 |
| 5,984,100 | A | | 11/1999 | Ramsey et al. | |
| 6,383,457 | B1 | | 5/2002 | Brown | |
| D471,393 | S | | 3/2003 | Hutchinson | |
| 6,729,470 | B2 | | 5/2004 | Watlington | |
| 7,328,792 | B1 | | 2/2008 | Benson | |
| D586,166 | S | | 2/2009 | Hayes | |
| 2011/0253180 | A1 | | 10/2011 | Davidson | |

* cited by examiner

Primary Examiner — Kiet T Nguyen

(57) ABSTRACT

An apparatus for storing and sanitizing a plunger is presented. The apparatus first has an elongate body that has a first inner compartment and a door that is removably attached to said bod. Further, the apparatus has an illuminating element that is removably attached to an inside surface of the door and configured to sanitize said plunger when said plunger is located inside the inner compartment of said elongate body. The apparatus has a shelving unit separating the first inner compartment from a second inner compartment with a tray being removably coupled to the second inner compartment. The apparatus has a plurality of drain holes for draining liquid. To secure the door a first magnetic tab is located on the inside surface of the door and a second magnetic tab is located on a right side of the elongate body. The first magnetic tab is configured to mate with the second magnetic tab for securing the door in a closed configuration. The door has a door knob.

10 Claims, 1 Drawing Sheet

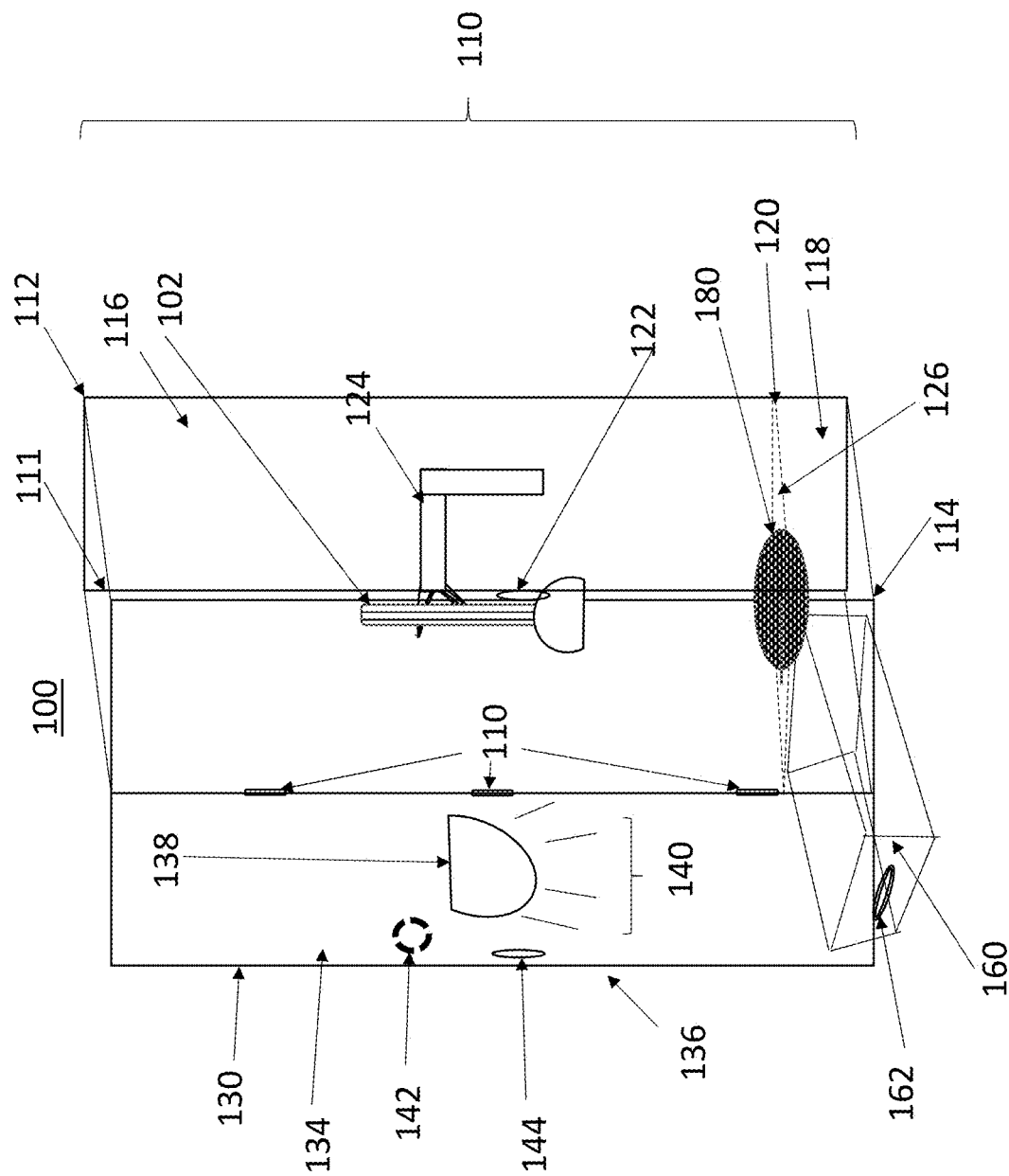

STORAGE UNIT FOR A PLUNGER

FIELD OF THE INVENTION

This invention relates to storage units. More particularly, it relates to storage units with drains.

BACKGROUND

The present invention is related to a storage unit for plungers and the like. More particularly, the present invention is related to a convenient plunger storage unit which is economically manufactured and which can accept multiple plunger types.

Plungers are well known commercially available items found in most homes. Plungers serve the function of applying some type of force to a clogged drain such that the force displaces the clog allowing the drain to flow freely. Most plungers have a handle and either a bell or some other volume displacement mechanism.

One common problem with plungers is storage. It would be readily apparent that plungers are unsanitary owing to their use in clogged toilets, sinks and the like. Furthermore, plungers are typically wet with unsanitary water. There has been a long-standing desire for a plunger storage unit which is capable of trapping drippings from a plunger and which is aesthetically pleasing.

A particular problem with plunger storage is the wide variety of sizes, shapes and configurations. Previously a storage unit would only house a limited number of plunger designs. This led to a proliferation of plunger storage units none of which were very successful since the market for each was limited. There has been a long-felt need for a plunger storage unit which can be easily modified, by the eventual consumer, to fit multiple and diverse plungers.

BRIEF DESCRIPTION OF THE DRAWINGS

FIG. 1 is an illustrated exemplary apparatus to store and sanitize a plunger.

DETAILED DESCRIPTION

The phrases "in one embodiment," "in various embodiments," "in some embodiments," and the like are used repeatedly. Such phrases do not necessarily refer to the same embodiment. The terms "comprising," "having," and "including" are synonymous, unless the context dictates otherwise. Such terms do not generally signify a closed list.

"Above," "adhesive," "affixing," "any," "around," "both," "bottom," "by," "comprising," "consistent," "customized," "enclosing," "friction," "in," "labeled," "lower," "magnetic," "marked," "new," "nominal," "not," "of," "other," "outside," "outwardly," "particular," "permanently," "preventing," "raised," "respectively," "reversibly," "round," "square," "substantial," "supporting," "surrounded," "surrounding," "threaded," "to," "top," "using," "wherein," "with," or other such descriptors herein are used in their normal yes-or-no sense, not as terms of degree, unless context dictates otherwise.

Reference is now made in detail to the description of the embodiments as illustrated in the drawings. While embodiments are described in connection with the drawings and related descriptions, there is no intent to limit the scope to the embodiments disclosed herein. On the contrary, the intent is to cover all alternatives, modifications and equivalents. In alternate embodiments, additional devices, or combinations of illustrated devices, may be added to, or combined, without limiting the scope to the embodiments disclosed herein.

Referring to FIG. 1, an exemplary apparatus 100 for storing and sanitizing a plunger is described. The apparatus 100 is useful to have a safe, secure storage for a plunger which may have been used and do not want others to play or handle an unsanitized plunger 102. Another use is to have the apparatus 100 sanitize the plunger 102 as it is stored in the apparatus.

The apparatus 100 has an elongated body 110. The elongated body 110 may have any dimensions and shape as desired. Preferably, the elongated body 110 is thirty inches (30") in height, eight and one-half inches (8.5") in width and eight and one-half inches (8.5") deep. The apparatus 100 may be made of any material, but is preferably plastic such that cleaning and sanitizing of the apparatus 100 is easier.

The elongated body 110 has a top 112, a bottom 114, a first compartment 116 and a second compartment 118. The bottom 114 may have wheels or legs (no shown) attached in an alternative embodiment. The elongated body 110 has a door 130. The door 130 is coupled to the elongated body 110 on one side by a plurality of hinges 132. The door 130 is removable and is adjustable.

The door 130 has an inside surface 134 and an outside surface 136. The inside surface 134 has an illuminating element 138. The illuminating element 138 is useful for providing light to the first compartment 116 of the elongated body 110 and the second compartment 118 of the elongated body 110. The illuminating element may have a lamp which may be ultra-violet, LED, LCD, etc. The illuminating element 138 may be automatic, that is by sensing motion it may provide energy to the lamp or it may be manual. The illuminating element 138 may be removably attached to the inside surface 134 of the door 130. The illuminating element 138 is preferably battery powered but may also be powered using solar energy, electric outlets, etc.

The illuminating element 138 may also have spraying mechanisms to spray sanitizing spray 140 into the first compartment 116 of the elongated body 110. The sanitizing spray 140 is useful to sanitize the plunger 102 without having manual interactive of handling an unsanitized plunger 102. The plunger 102 has a plunger holder 124. The plunger holder 124 may be any shape and is useful in holding the plunger 102 in a position for the sanitizing spray 140 to have access to the plunger 102.

The door 130 has a door knob 142 and a first magnet tab 144. The door knob 142 is positioned on the outside surface 136 of the door 130. The first magnetic tab 144 is position on the inside surface 134 of the door 130. The elongated body 110 has a second magnetic tab 122. The second magnetic tab 122 allows the door 130 to be secure when in the closed position by coupling with the first magnetic tab 144 of the door 130. The first magnetic tab 144 of the door 130 and the second magnetic tab 122 of the elongated body 110, situated on a right-hand side 111 of the elongated body, are configured to mate to secure the door 130 in a closed configuration.

The elongated body 110 has a shelving unit 120 to separate the first compartment 116 and the second compartment 118. The shelving unit 120 is preferably six inches (6") from the bottom 114 of the elongated body 110.

A tray 160 is provided to catch unsanitary elements or dirt. The tray 160 may be any size and shape but must be able to fit in the second compartment 118 of the elongated body. The tray 160 has a handle 162 to provide a ease of inserting or removing the tray 160 from the second compartment 118 of the elongated body 110.

The apparatus 100 also has a plurality drain holes 180. The plurality of drain holes 180 are located on a top 126 of the shelving unit 120. Preferably, the plurality of drain holes 180 are located equal distance, thus centrally located, on the shelving unit 120. The plurality of drain holes 180 are useful in draining liquid from the shelving unit 120 into the tray 160.

In the numbered clauses below, specific combinations of aspects and embodiments are articulated in a shorthand form such that (1) according to respective embodiments, for each instance in which a "component" or other such identifiers appear to be introduced (with "a" or "an," e.g.) more than once in a given chain of clauses, such designations may either identify the same entity or distinct entities; and (2) what might be called "dependent" clauses below may or may not incorporate, in respective embodiments, the features of "independent" clauses to which they refer or other features described above.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

The features described with respect to one embodiment may be applied to other embodiments or combined with or interchanged with the features of other embodiments, as appropriate, without departing from the scope of the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for storing and sanitizing a plunger, said apparatus comprising:
   an elongate body having a first inner compartment;
   a door, said door being removably attached to said body;
   an illuminating element, said illuminating element removably attached to an inside surface of said door and configured to sanitize said plunger when said plunger is located inside said inner compartment of said elongate body;
   a shelving unit, said shelving unit separating said first inner compartment from a second inner compartment;
   a tray, said tray being removably coupled to said second inner compartment;
   a plurality of drain holes, said plurality of drain holes located on said shelving unit;
   wherein said plurality of drain holes are configured to drain liquid from said shelving unit to said tray;
   a first magnetic tab, said first magnetic tab located on said inside surface of said door;
   a second magnetic tab, said second magnetic tab located on a right side of said elongate body;
   a door knob, said door knob located on an outside surface of said door; and
   wherein said first magnetic tab is configured to mate with said second magnetic tab for securing the door in a closed configuration.

2. The apparatus of claim 1, wherein said door is hingedly attached to said body.

3. The apparatus of claim 1, wherein said illuminating element is battery-powered.

4. The apparatus of claim 1, wherein said illuminating element comprises ultraviolet light.

5. The apparatus of claim 1, wherein said plurality of drain holes is located in a central portion of said shelving unit.

6. The apparatus of claim 1, wherein said apparatus is made of a plastic material.

7. The apparatus of claim 1, wherein said apparatus is approximately 30 inches in height.

8. The apparatus of claim 1, wherein said apparatus is approximately 8.5 inches in width.

9. The apparatus of claim 1, wherein said apparatus is approximately 8.5 inches deep.

10. The apparatus of claim 1, wherein said shelving unit is approximately 6 inches higher than a bottom surface of said elongate body.

\* \* \* \* \*